(12) United States Patent
Tomii

(10) Patent No.: US 7,243,051 B2
(45) Date of Patent: Jul. 10, 2007

(54) SYSTEM FOR PREDICTING THREE-DIMENSIONAL STRUCTURE OF PROTEIN

(75) Inventor: Kentaro Tomii, Tokyo (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/540,736

(22) PCT Filed: Dec. 26, 2003

(86) PCT No.: PCT/JP03/16982

§ 371 (c)(1),
(2), (4) Date: Jul. 28, 2005

(87) PCT Pub. No.: WO2004/059557

PCT Pub. Date: Jul. 15, 2004

(65) Prior Publication Data

US 2005/0267687 A1 Dec. 1, 2005

(30) Foreign Application Priority Data

Dec. 26, 2002 (JP) .............................. 2002-377704
Dec. 5, 2003 (JP) .............................. 2003-406776

(51) Int. Cl.
*G06F 15/00* (2006.01)

(52) U.S. Cl. ...................... 702/196; 702/196; 702/189; 702/155; 703/11; 436/86; 436/89; 424/484; 73/432.1

(58) Field of Classification Search ................ 702/155, 702/189, 196; 703/11; 436/86, 89; 424/484; 73/432.1

See application file for complete search history.

(56) References Cited

U.S. PATENT DOCUMENTS 5,436,850 A * 7/1995 Eisenberg et al. ............ 703/11

(Continued)

FOREIGN PATENT DOCUMENTS

JP 2002-358309 A 12/2002

OTHER PUBLICATIONS

Adams et al., 'A New Method for Evaluating the Structural Similarity of Proteins Using Geometric Morphometrics', Dec. 1999, Adams & Naylor, No. 16, pp. 1-2.*

(Continued)

*Primary Examiner*—Marc S. Hoff
*Assistant Examiner*—Elias Desta
(74) *Attorney, Agent, or Firm*—Darby & Darby

(57) ABSTRACT

The present invention is to provide a system for measuring the similarity between protein profile matrices which is suitably used for predicting a protein three-dimensional structure. The present invention provides a system for measuring the similarity between protein profile matrices, wherein said profile matrix consists of a group of profile columns containing occurrence probabilities every amino acid type at a respective locations of amino acid residues in a multiple alignment in which amino acid sequences in a plurality of related proteins are aligned in multiple, said system for measuring the similarity comprises (a) means for preparing two profile matrices of a query profile matrix and a subject profile matrix; (b) means for calculating correlation coefficients between the respective profile columns in said query profile matrix and the respective profile columns in said subject profile matrix with respect to full or partial combinations of both the respective profile columns; and (c) means for forming a score matrix consisting of said correlation coefficients.

5 Claims, 5 Drawing Sheets

U.S. PATENT DOCUMENTS 6,321,164 B1 * 11/2001 Braun et al. .................. 702/22
2005/0170372 A1 * 8/2005 Afeyan et al. ................. 435/6

OTHER PUBLICATIONS

Holm et al., 'Dali/FSSP Classification of Three-demensional Protein Folds', 1997, Oxford University Press, vol. 25, No. 1, pp. 231-234.*

Pazos et al., 'CABIOS Application Note: A graphical Interface for Correlated Mutations and Other Protein Structure Prediction Methods', 1997, Oxford University Press, vol. 13, No. 3, pp. 319-321.*

Kubitscheck et al., 'Three-Dimensional Diffusion Measurements by Scanning Microphotolysis', Nov. 1988, JOM, vol. 192, Pt. 2, pp. 126-138.*

Dinakarpandian et al., 'BIOMIND-Protein Property Prediction by Property Proximity Profiles', 2002, UMKC Publication, pp. 168-172.*

"Within the Twilight Zone: A Sensitive Profile-Profile Comparison Tool Based Information Theory", by Yona, G. Levitt, M., Journal of Molecular Biology, Feb. 1, 2002, vol. 315, Issue 5, pp. 1257-1275; especially, pp. 1259-1260 [on line]retrieved on Jan. 29, 2004, Retrieved from: <URL=http://www.cs.cornell.edu/golan/Papers/jmb02.pdf>.

"Comparison of sequence profiles. Strategies for structural predictions using sequence information", by Rychlewski, L. et al., Protein Science, Feb. 2000, vol. 9, Issue 2, pp. 232-241 [online][retrieved on Jan. 29, 2004], retrieved from <http://www.proteinscience.org/cgl/reprint/9/2/232.pdf>.

Patent Abstracts of Japan for JP2002-358309 published Dec. 13, 2002.

International Search Report for PCT/JP2003/016982 mailed Feb. 10, 2004.

* cited by examiner

Reliability

SYSTEM FOR PREDICTING THREE-DIMENSIONAL STRUCTURE OF PROTEIN

CROSS-REFERENCE TO PRIOR APPLICATION

This is a U.S. National Phase application under 35 U.S.C. 371 of International Patent Application No. PCT/JP2003/016982, filed Dec. 26, 2003, and claims the benefit of Japanese Patent Application No. 2002-377704, filed Dec. 26, 2002 and 2003-406776, filed Dec. 5, 2003, all of which are incorporated by reference herein. The International Application was published in Japanese on Jul. 15, 2004 as WO 2004/059557 A1 under PCT Article 21(2).

FIELD OF ART

The present invention relates in general to a system for measuring the similarity between protein profile matrices and, more particularly, to a system for measuring the similarity between protein profile matrices which is suitably used for predicting a protein three-dimensional structure.

BACKGROUND ART

Proteins in the natural world had been selected in the process of evolution and gotten to reveal specific functions. It is known that these functions of proteins depend on their three-dimensional structures. Thus, if it is possible to predict the three-dimensional structure of a protein, its functions would be predictable.

In the past, in order to investigate a protein on which no information has been ever obtained, people has wanted methods for inferring or predicting its tertiary structure by computationally determining the similarity to proteins whose tertiary structures were already known. As a powerful one out of such methods, there is known a method of comparing protein profile matrices (Rychlewski L, Jaroszewski L, Li W, Godzik A. *Protein Sci.* February (2000); 9(2): 232-41).

Here, a protein profile matrix is obtained by transforming the occurrence frequencies of types of amino acids in related proteins (protein family etc.) into numerical values, for every location of amino acid residues, to form a matrix. The matrix is usually formed through the following steps. Firstly, given a multiple alignment in which amino acid sequences in a plurality of related proteins are juxtaposed in multiple, the occurred numbers of each type of 20 amino acids are counted for every location of amino acid residues in the multiple alignment. Thus-counted numbers are then normalized to be transformed into the occurrence probabilities. At this time, the occurred numbers are revised with consideration for weights depending on mutual similarities between amino acid sequences in the members of a given multiple alignment. Then, a profile matrix is formed.

Here, a multiple alignment is obtained by juxtaposing amino acid sequences in a plurality of biologically mutually-related proteins with aligning the amino acid residues which are considered to correspond to each other. A multiple alignment may be readily prepared, for example, by using the existing program PSI-BLAST (Altschul et al., *Nucleic Acids Res.* (1997) 25(17):3389-3402) and searching the sequence database for a certain sequence as a query, or by using the existing program CLUSTALW (Higgins D., Thompson J., Gibson T. Thompson J. D., Higgins D. G., Gibson T. J. (1994). *Nucleic Acids Res.* 22:4673-4680) with queries of a group of amino acid sequences in a plurality of biologically mutually-related proteins. It may be also prepared based on the results of tertiary structure comparison and the like.

Table 1 schematically shows a multiple alignment prepared on the basis of a protein in which an amino acid sequence has a length n (the number of amino acid residues). Note that, in Table 1, the first column shows the names of proteins, the numbers "1 to n" in the first row designate the locations of amino acid residues in the multiple alignment, and each of the alphabet letters is the one-letter code of each type of amino acid.

TABLE 1

|                  | 1 | 2 | 3 | 4 | 5 | 6 | 7 | 8 | ... | n |
|------------------|---|---|---|---|---|---|---|---|-----|---|
| 20807455/14-218  | M | I | D | H | T | L | L | K | ... | G |
| 19551629/13-215  | I | L | D | Y | T | L | L | G | ... | A |
| 16974933/15-229  | L | M | D | L | T | T | L | N | ... | A |
| 16120769/20-234  | L | M | D | L | T | T | L | N | ... | A |

Although amino acids are present at all of the illustrated locations of amino acid residues in the example of Table 1, a gap may be designated by "• (a dot)" in case that a location of amino acid residue is not occupied by the corresponding amino acid residue. Table 2 schematically shows a profile matrix formed based on a multiple alignment having a length n which is obtained in Table 1. In Table 2, the first column shows types of amino acids (which may include gaps) and the numbers "1 to n" in the first row designate the locations of amino acid residues in the profile matrix.

TABLE 2

| AA/Pos. | 1 | 2 | 3 | ... | n |
|---------|------|------|------|-----|------|
| A | 0.00 | 0.00 | 0.00 | ... | 0.71 |
| R | 0.00 | 0.00 | 0.00 | ... | 0.00 |
| N | 0.00 | 0.00 | 0.00 | ... | 0.00 |
| D | 0.00 | 0.00 | 0.96 | ... | 0.00 |
| C | 0.00 | 0.00 | 0.00 | ... | 0.00 |
| Q | 0.00 | 0.00 | 0.00 | ... | 0.00 |
| E | 0.00 | 0.00 | 0.04 | ... | 0.00 |
| G | 0.00 | 0.00 | 0.00 | ... | 0.29 |
| H | 0.00 | 0.00 | 0.00 | ... | 0.00 |
| I | 0.29 | 0.29 | 0.00 | ... | 0.00 |
| L | 0.41 | 0.29 | 0.00 | ... | 0.00 |
| K | 0.00 | 0.00 | 0.00 | ... | 0.00 |
| M | 0.29 | 0.41 | 0.00 | ... | 0.00 |
| F | 0.00 | 0.00 | 0.00 | ... | 0.00 |
| P | 0.00 | 0.00 | 0.00 | ... | 0.00 |
| S | 0.00 | 0.00 | 0.00 | ... | 0.00 |
| T | 0.00 | 0.00 | 0.00 | ... | 0.00 |
| W | 0.00 | 0.00 | 0.00 | ... | 0.00 |
| Y | 0.00 | 0.00 | 0.00 | ... | 0.00 |
| V | 0.01 | 0.01 | 0.00 | ... | 0.00 |

Each column in the profile matrix shows a distribution of occurrence probabilities as to all types of amino acids at each of the locations of amino acid residues in a plurality of related proteins. Table 3 lo schematically shows a profile column at a residue location "2" in the profile matrix shown in Table 2.

TABLE 3

| Location 2 |
|------------|
| 2          |
| 0.00       |
| 0.00       |
| 0.00       |

TABLE 3-continued

Location 2

0.00
0.00
0.00
0.00
0.00
0.00
0.29
0.29
0.00
0.41
0.00
0.00
0.00
0.00
0.00
0.00
0.01

From this it follows that, at a residue location "2" in the profile matrix shown in Table 2, the revised occurrence probability of alanine (A) is 0.00 and the revised occurrence probability of methionine (M) is 0.41.

In the past, in order to compare and/or align two profile matrices or two amino acid sequences, Dynamic Programming (Needleman S B, Wunsch C D, *J Mol Biol*. (1970) March; 48(3): 443-53) has been employed. When preparing an alignment, in a pair of amino acid sequences or a pair of profile matrices to be compared, it is necessary to determine which residues or profile columns should form a parallel to each other (in this case, it may happen that a residue and a gap form a parallel to each other), and there are a great number of thinkable ways for making them form a parallel to each other. Dynamic Programming is an algorithm capable of automatically and efficiently finding out such a paralleling way as maximizes a similarity score out of these ways. The result itself obtained by the said paralleling way is an alignment that is to be finally wanted.

Dynamic Programming requires inputs composed of two amino acid sequences to be compared and a score matrix consisting of similarity scores (marks indicating degrees of similarity) for the respective pairs of residues between two amino acid sequences to be paralleled in the case of a usual amino acid sequence comparison, or inputs composed of two model amino acid sequences to be compared and a score matrix consisting of similarity scores for the respective pairs of profile columns between two profile matrices to be paralleled in the case of a profile matrix comparison. According to these inputs, Dynamic Programming outputs an alignment of a pair of amino acid sequences to be compared and its final scores (the scores obtained by finding such an optimal path as gives the maximum similarity score) in the case of a usual amino acid sequence comparison, or an alignment of a pair of model amino acid sequences to be compared and its final scores in the case of a profile matrix comparison.

Thus, in order to compare profile matrices by a method employing Dynamic Programming, it is necessary to form a score matrix which measures with high accuracy the similarity between two profile matrices to be compared.

As one of the methods for calculating a score matrix which indicates the degree of similarity between two profiles, there is known a method developed by Rychlewski et al. (Rychlewski et al. (2000), 9:p232-241). This method comprises the steps of calculating, as the value of a similarity score between a pair of profile columns to be paralleled, a dot product of the said pair of profile columns and then forming a score matrix between two profile matrices to be compared.

For example, given two profile matrices $X=x_1x_2 \ldots x_n$ (wherein $x_p \ldots$ designates a profile column at a location p of an amino acid residue) and $Y=y_1y_2 \ldots y_q \ldots y_m$ (wherein $y_q$ designates a profile column at a location q of an amino acid residue), a similarity score $D_{qp}$ (a similarity score between a profile column $x_p$ and a profile column $y_q$), which is a component of a score matrix of n rows and m columns, is represented by the following equation:

$$D_{pq} = \sum_{a}^{j} x_{pa} y_{qa}$$

wherein $x_{pa}$ designates a component of a profile column $x_p$, $y_{qa}$ designates a component of a profile column $y_q$, and j is the number of components in a profile column (usually 20).

According to the above-described method, in the case wherein there are only a quite limited types of occurred residues and a weak generation of amino acid substitution in both of a pair of profile columns to be paralleled, the dot product has such a high numeral value as to give a high similarity score. Such a residue location, which is highly conservative because of occurred residues of quite limited types and a weak generation of amino acid denaturation, is considered to be a highly conservative place from functional or physicochemical needs in vivo and also a biologically important location. In such a region, it is considered that the above-described method makes it possible to measure the similarity with high accuracy.

However, according to the above-described method, there was a possibility of measuring with high accuracy a location where types of occurred residues are limited, while there was a problem that it was impossible to measure with high accuracy such a region as generates heavy amino acid substitution but seems to have a commonness in its substituting pattern, such as a non-conservative location which exists in a motif, a location which is meaningfully exposed in a protein's tertiary structure and has a large significance only in its polarity, a location which exists, contrarily, in an embedded portion of the tertiary structure and is conservative with regard to only its hydrophobicity, and so on, even though it is a biologically important location.

In addition, because it was required that the average of all the components (similarity scores) in a score matrix has a negative value and the standard deviation is almost constant, the similarity scores had to be normalized. Thus, there was also a problem of being troublesome.

Therefore, it has been desired to develop a highly accurate and simple method for measuring the similarity between profile matrices at not only conservative regions but also non-conservative regions.

DISCLOSURE OF THE INVENTION

An object of the present invention is to provide a system for measuring the similarity between protein profile matrices for the sake of predicting a protein three-dimensional structure.

Specifically, the present invention provides a system for measuring the similarity between protein profile matrices, a system for predicting a protein three-dimensional structure, a program for enabling a computer to function as any of these systems, a computer-readable recording medium in which the program is stored, and so on, as described in the following.

(1) A system for measuring the similarity between protein profile matrices in order to predict the three-dimensional structure of a protein, wherein said profile matrix consists of a group of profile columns containing occurrence probabilities every amino acid type at a respective locations of amino acid residues in a multiple alignment in which amino acid sequences in a plurality of related proteins are aligned in multiple, said system for measuring the similarity comprises the following means:

(a) means for preparing two profile matrices of a query profile matrix formed based on a plurality of proteins including proteins having three-dimensional structures to be predicted and a subject profile matrix formed based on a plurality of proteins having known three-dimensional structures;

(b) means for calculating correlation coefficients between the respective profile columns in said query profile matrix and the respective profile columns in said subject profile matrix with respect to full or partial combinations of both the respective profile columns; and (c) means for forming a score matrix consisting of said correlation coefficients.

(2) A system for predicting a protein three-dimensional structure characterized in using a score matrix formed through a system set forth in item (1) above.

(3) A program for enabling a computer to function as a system for measuring the similarity between protein profile matrices in order to predict a protein three-dimensional structure, wherein said profile matrix consists of a group of profile columns containing occurrence probabilities every amino acid type at a respective locations of amino acid residues in a multiple alignment in which amino acid sequences in a plurality of related proteins are aligned in multiple, said system for measuring the similarity comprises the following means:

(a) means for preparing two profile matrices of a query profile matrix formed based on a plurality of proteins including proteins having three-dimensional structures to be predicted and a subject profile matrix formed based on a plurality of proteins having known three-dimensional structures;

(b) means for calculating correlation coefficients between the respective profile columns in said query profile matrix and the respective profile columns in said subject profile matrix with respect to full or partial combinations of both the respective profile columns; and (c) means for forming a score matrix consisting of said correlation coefficients.

(4) A computer-readable recording medium storing a program set forth in item (3) above.

(5) A method of measuring the similarity between protein profile matrices, wherein said profile matrix consists of a group of profile columns containing occurrence probabilities every amino acid type at a respective locations of amino acid residues in a multiple alignment in which amino acid sequences in a plurality of related proteins are aligned in multiple, said method of measuring the similarity comprises the following steps:

(a) a step of preparing two profile matrices of a query profile matrix and a subject profile matrix;

(b) a step of calculating correlation coefficients between the respective profile columns in said query profile matrix and the respective profile columns in said subject profile matrix with respect to full or partial combinations of both the respective profile columns; and (c) a step of forming a score matrix consisting of said correlation coefficients.

(6) A method of measuring the similarity set forth in item (5) above, wherein said subject profile matrix is a profile matrix formed based on a plurality of proteins having known three-dimensional structures, and said query profile matrix is a profile matrix formed based on a plurality of proteins including proteins having three-dimensional structures to be predicted.

(7) A method of predicting a protein three-dimensional structure characterized in using a score matrix obtained in item (5) or (6) above.

According to the present invention, it is possible to measure the similarity between protein profile matrices simply and easily with high accuracy. A score matrix obtained by the present invention is suitably usable for predicting a protein three-dimensional structure.

BEST MODE FOR CARRYING OUT THE INVENTION

The present invention will be explained in detail below.

1. System for Measuring Similarity

Figure 1:
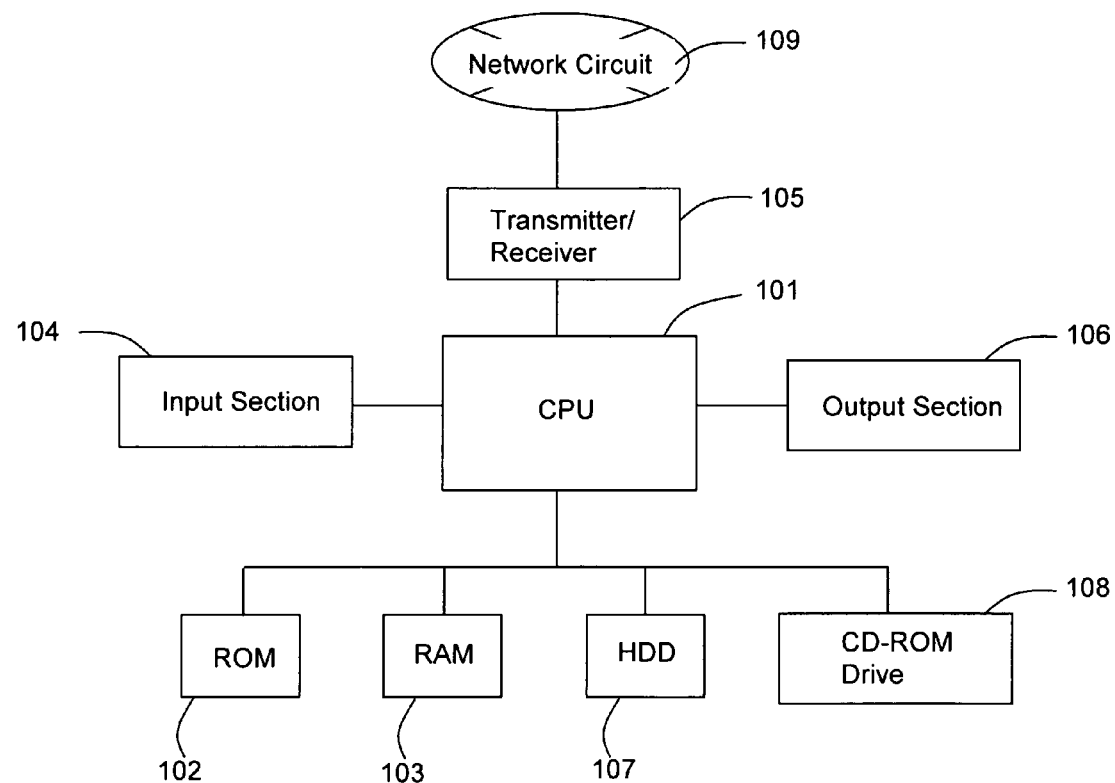
FIG. 1 is a block diagram showing a hardware formation employed in an embodiment of the present invention.

FIG. 1 is a block diagram showing a hardware formation employed in an embodiment of the present invention.

As shown in FIG. 1, a system for measuring the similarity according to the present invention comprises a CPU 101, a ROM 102, a RAM 103, an input section 104, an information-communicating transmitter/receiver section 105, an output section 106, a hard disk drive (HDD) 107, a CD-ROM drive 108, etc.

CPU 101 controls the system for measuring the similarity in its totality according to programs stored in an information memory means (e.g., a magnetic and/or optical recording medium), and receives information from input section 104 and others and sends it to output section 106. It may also perform measuring processes according to information received through a network circuit 109. Input section 104 may be a keyboard or a mouse which is operated in order to input conditions or data required for performance of the measuring processes. ROM 102 stores programs and the like which command the processing necessary for operation of the system for measuring the similarity according to the present invention. RAM 103 temporarily stores data necessary for the system for measuring the similarity to conduct the processing.

Transmitter/receiver section 105 performs information communication (data transmitting and receiving processes) with network circuit 109 and others according to commands from CPU 101 and comprises, for example, a modem, a router, etc. Output section 106 processes and displays, according to commands from CPU 101, information inputted by input section 104 such as profile data, other various conditions, etc. (e.g., a display, a printer, etc.). CD-ROM drive 108 reads out programs, data and the like for operation of the system for measuring the similarity, which are stored in a CD-ROM, and then stores them in, for example, RAM 103 according to commands from CPU 101. As a recording medium other than a CD-ROM, a writable/erasable CD-R or CD-RW may be used. In this case, a CD-R drive or CD-RW drive may be provided instead of CD-ROM drive 108. Other than these media, a DVD or MO and its medium may be used and the corresponding drive means may be provided.

Programs for enabling a computer to operate the system for measuring the similarity according to the present invention may be written in C languages or such. Thus, this software can cooperate with a variety of operating systems such as Windows (registered trademark) 95/98/2000, Linux (registered trademark), UNIX (registered trademark), and so on.

Figure 2:
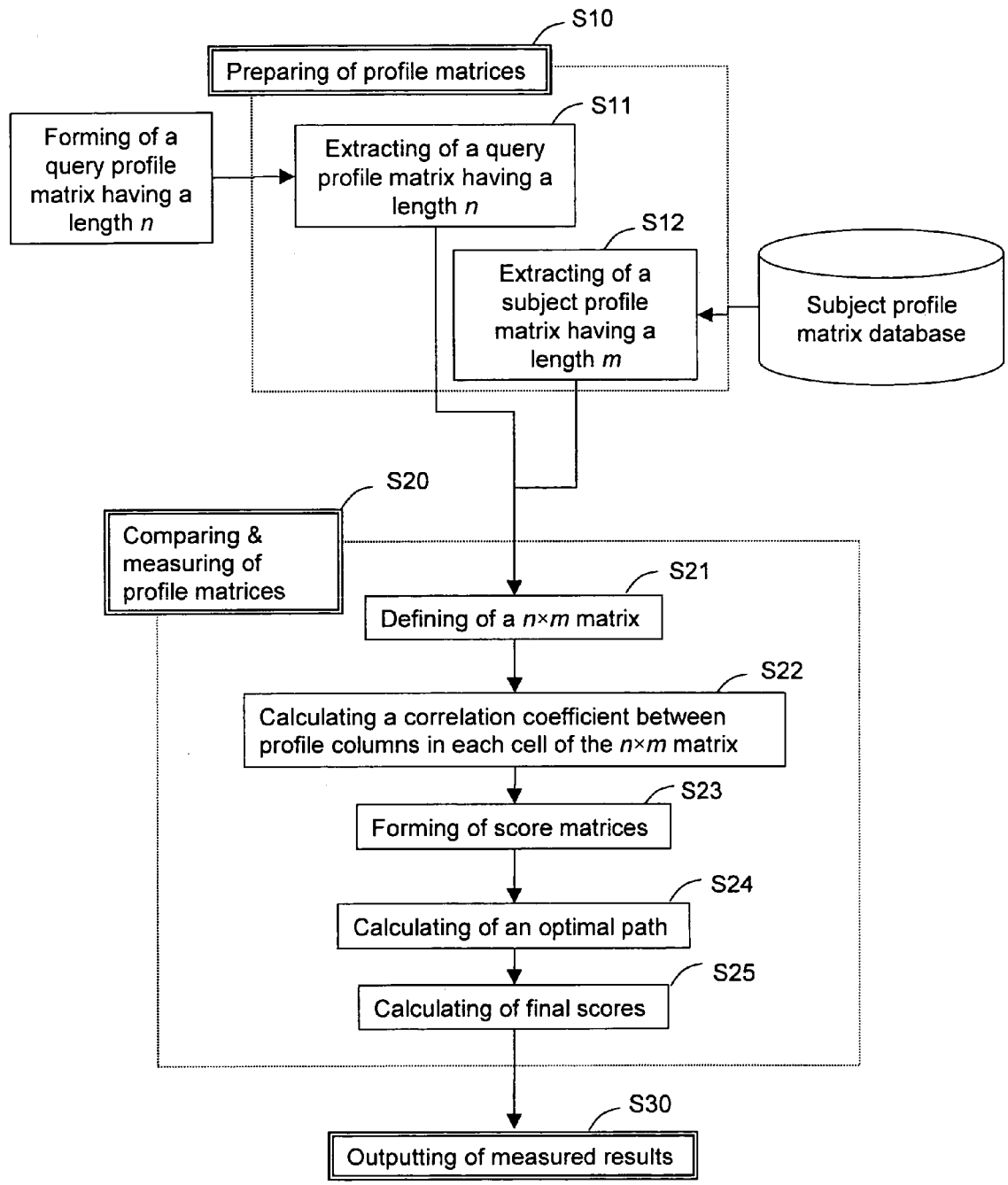
FIG. 2 is a flow chart showing an example of procedures including those in a system for measuring the similarity between profile matrices according to the present invention.

FIG. 2 is a flow chart showing an example of procedures including those in a system for measuring the similarity between profile matrices according to the present invention.

As shown in FIG. 2, a system for measuring the similarity between profile matrices according to the present invention firstly prepares two profile matrices to be compared (a query profile matrix and a subject profile matrix), then measures the similarity between them, and outputs the measured results at need.

Each of the processing steps will be explained in detail below.

(a) Preparation of Profile Matrices (S10)

In the step of preparing profile matrices, two profile matrices to be compared are prepared (extracted) (S11 and S12). Here, one (a subject profile matrix) of the two profile matrices is a profile matrix (having a length m in FIG. 2) which has been formed based on a plurality of proteins having known three-dimensional structures. The other (a query profile matrix) is preferably a profile matrix (having a length n in FIG. 2) which has been formed based on a plurality of proteins including a protein having a three-dimensional structure to be predicted (whether its tertiary structure is known or unknown).

A method of forming a profile matrix may be one of the above-described known methods and is not specially limited. For example, using one of the existing programs, PSI-BLAST, a search may be made through the sequence databases with inputting a certain sequence so as to make a multiple alignment, and then a profile matrix may be formed based on the multiple alignment. Also, inputting a group of amino acid sequences in a plurality of biologically related proteins, a multiple alignment may be made through one of the existing programs, CLUSTALW, and then a profile matrix may be formed based on the said multiple alignment. Inputting a preliminarily prepared multiple alignment, a profile matrix may be also formed based on this multiple alignment.

Here, a profile matrix may be formed based on the whole of sequence in a model amino acid sequence, or it may be also formed based on a partial region, such as a motif region etc., in a model sequence. When making a multiple alignment, empirically-derived gap penalties may be also introduced.

As a profile matrix, if necessary, there may be also used a matrix formed from occurrence frequencies of types of amino acids divided by random occurrence frequencies of the corresponding types of amino acids (PSSM: Gribskov, M., et al. (1987) *Proc. Natl. Acad. Sci.* USA, 84, 4355-4358).

For example, using a protein having a three-dimensional structure to be predicted as a model amino acid sequence, a query profile matrix can be prepared based on this sequence. Further, using, as a model sequence, the amino acid sequence of a protein acquired from a protein structure classification database such as, for example, SCOP (Murzin et al., *J. Mol. Biol.* 247(4): 536-540 (1995) and CATH (Orengo et al., *Structure* 5(8): 1093-1108 (1997)), a subject profile matrix can be prepared based on this sequence. It is preferred that thus-obtained subject profile matrices have been previously formed for every model sequence and then stored as a subject profile matrix database.

(b) Calculation of Correlation Coefficients (Comparing & Measuring of Profile Matrices) (S20)

Next, in the steps of measuring the similarity between profile matrices, the similarities between the respective profile columns in the query profile matrix prepared in the step described above and the respective profile columns in the subject profile matrix are measured for every pair of columns.

Figure 3:
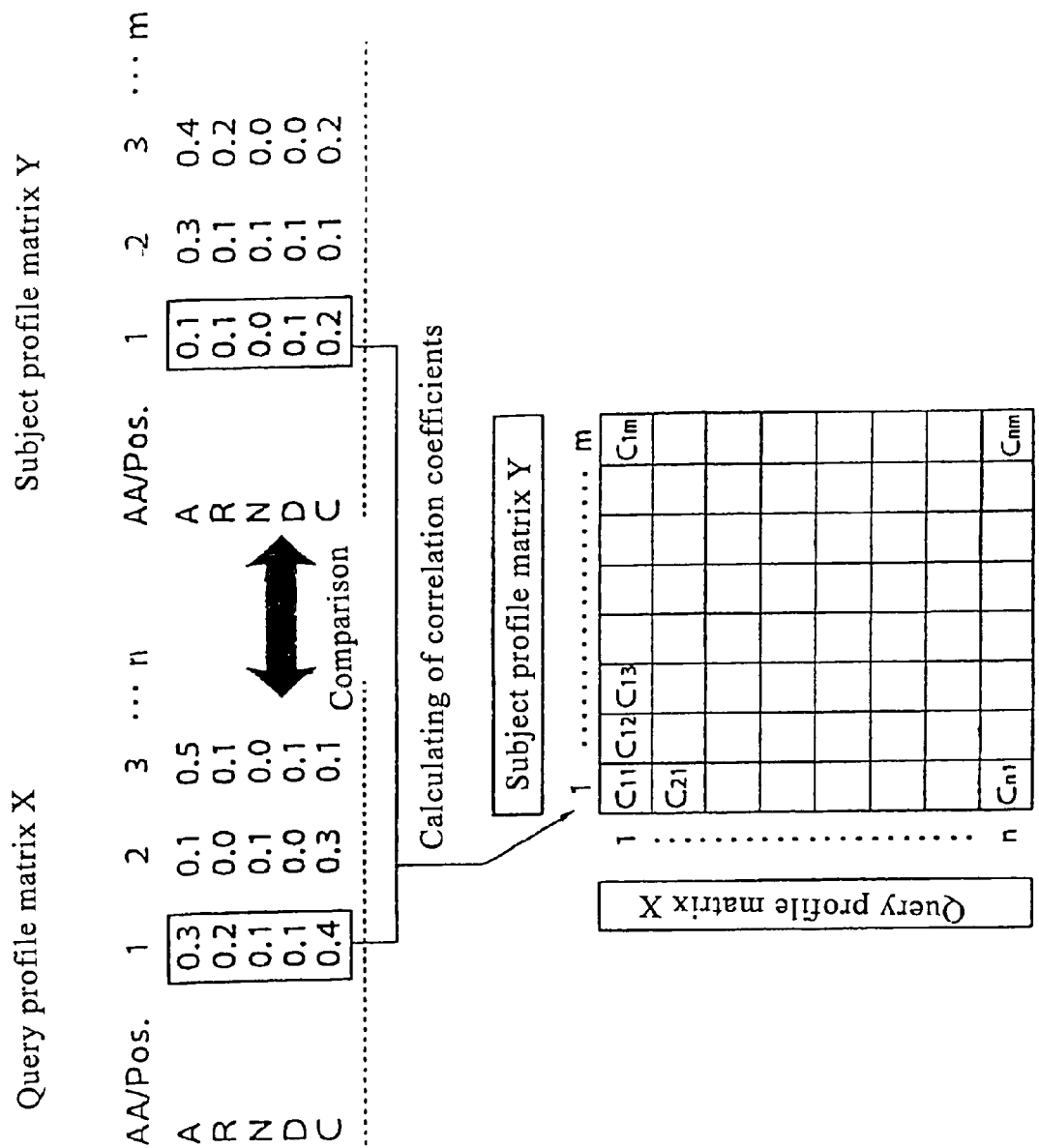
FIG. 3 is a schematic diagram illustrating the steps for measuring the similarity for every pair of profile columns and forming a score matrix in a system for measuring the similarity between profile matrices according to the present invention.

FIG. 3 is a schematic diagram illustrating the steps of measuring the similarity for every pair of profile columns and forming a score matrix based on the measured results.

According to the present invention, the similarity between profile columns is estimated by calculating correlation coefficients between profile columns.

For example, representing a query profile matrix by $X = x_1 x_2 \ldots x_p \ldots x_n$ (wherein $x_p$ designates a profile column at a location p of a amino acid residue) and a subject profile matrix by $Y = y_1 y_2 \ldots y_q \ldots y_m$ (wherein $y_q$ designates a profile column at a location q of a amino acid residue), a similarity score $C_{qp}$ between profile columns $x_p$ and $y_q$ is represented by the following equation:

$$C_{pq} = \frac{\sum_{a}^{j}(x_{pa} - \overline{x_p})(y_{qa} - \overline{y_q})}{\sqrt{\sum_{a}^{j}(x_{pa} - \overline{x_p})^2 \sum_{a}^{j}(y_{qa} - \overline{y_q})^2}}$$

wherein $x_{pa}$ designates a component of a profile column $x_p$,
$y_{qa}$ a component of a profile column $y_q$,
$\overline{x_p}$ an average value in a profile column $x_p$,
$\overline{y_q}$ an average value in a profile column $y_q$, and
j is the number of components in a profile column (usually 20).

In the present invention, the similarity between profile columns is estimated by the use of correlation coefficients between the profile columns. Thus, the similarity score takes a value between +1 and −1 in proportion to a degree of correlation between the profile columns. For example, when there is a correlation between the components of a pair of profile columns, i.e., there is a similarity between tendencies in amino acid substitution patterns, the correlation coefficient takes a value close to +1. On the other hand, when the respective components in a pair of profile columns take random values independently of each other, i.e., there is no correlation between tendencies in amino acid substitution patterns, the correlation coefficient takes a value of 0, and the correlation coefficient takes a value of −1 when tendencies in amino acid substitution patterns are directly opposite to each other. Thus, it is possible to make a very natural expression as to whether tendencies in amino acid substitution patterns are similar or non-similar to each other.

Therefore, according to the present invention, a high similarity score is obtained in a region showing a high correlation such as a conservative region where amino acid residues are highly conserved, that makes it possible to measure a similarity in such a conservative region with high accuracy.

Further, not only a region where amino acid residues are conserved, but the present invention makes it possible to measure a similarity with high accuracy also in such a region as could have never been processed by the prior method using a dot product in order to measure the similarity (Rychlewski et al.), for example, such a region as generates heavy amino acid substitution but is considered as a region where there is a commonness in substitution patterns, such as a non-conservative location which exists in a motif, a location which is meaningfully exposed in a protein's tertiary structure and has a large significance only in its polarity, a location which exists, contrarily, in an embedded portion of the tertiary structure and is conservative with regard to only its hydrophobicity, and so on.

For example, suppose we compare a pair of profile matrices containing zinc finger motifs of a certain type. The zinc finger motif is represented by:

C-[DES]-x-C-x(3)-I.

This representation shows that residues C, C and I are conserved at the $1^{st}$, $4^{th}$ and $8^{th}$ residue locations, respectively, D, E or S occurs at the $2^{nd}$ residue location, and especially any conserved residue is not present at $3^{rd}$, $5^{th}$, $6^{th}$ and $7^{th}$ residue locations. According to the prior method using a dot product for measuring the similarity, in this case, high scores are given at the $1^{st}$, $2^{nd}$, $4^{th}$ and $8^{th}$ residue locations, while only low scores are given at the other locations. From this it follows that the prior method using a dot product in order to measure the similarity is capable of measuring the similarity in a part of the motif, but incapable of measuring the similarity with high accuracy throughout the motif.

However, according to the present invention, not only high scores are given at the $1^{st}$, $2^{nd}$, $4^{th}$ and $8^{th}$ residue locations, but also at $3^{rd}$, $5^{th}$, $6^{th}$ and $7^{th}$ residue locations it is possible to measure the similarity with respect to such a substitution pattern that any conserved residue is specially not present, whereby high scores are given even at these residue locations. Therefore, the present invention makes it possible to measure the whole of pattern information throughout the motif.

In this connection, a similarity-measuring system according to the present invention is applicable over the full length of sequence in a protein having a three-dimensional structure to be predicted without being limited to a motif region. In other words, the said system can be also suitably applied in order to measure the similarity between profile matrices obtained with introduction of gap penalties.

In addition, the present invention can also show such a merit that because the values of average and standard deviation are approximately constant for the respective components (similarity scores) of a score matrix, there is no necessity for troublesome normalization of the similarity scores.

(c) Formation of Score Matrix

Correlation coefficients (similarity scores) between both of the respective profile columns are calculated with respect to full or partial combinations of both of the respective profile columns and then a score matrix is formed based on them. Thus-formed score matrix has rows where the number of rows is equal to the length of the query profile matrix and columns where the number of columns is equal to the length of the subject profile matrix in the case wherein similarity scores are calculated with respect to full combinations of both of the respective profile columns, and in the case wherein similarity scores are calculated with respect to partial combinations of both of the respective profile columns, it becomes a matrix which has columns and rows where the number of which is corresponding to the number of the said combinations.

In an example shown in FIG. 2, similarity scores are calculated with respect to full combinations of both of the respective profile columns. Since the query profile matrix has a length n and the subject profile matrix has a length m, similarity scores of m×n are generated (S22). Thus, the formed score matrix has n rows and m columns. The score matrix is formed by preliminarily defining a length of a profile matrix to be compared and a matrix corresponding to the number of calculated similarity scores (S21) and then inputting correlation coefficients between both of the respective profile columns in the respective columns of the defined matrix (S23).

The score matrix obtained according to the present invention allows the final scores between the two profile matrices (the similarity between the matrices) to be calculated with high accuracy. The final scores can be obtained through the known algorithm. For example, in the example shown in FIG. 2, inputting the respective model amino acid sequences in a pair of profile matrices to be compared and a score matrix between these profile matrices which is obtained according to the present invention, Dynamic Programming finds an optimal path (S24) and then seeks the final scores (S25).

The above-described operations are preferably performed with respect to all of the subject profile matrices stored in a subject profile matrix database.

2. Prediction of A Protein Three-Dimensional Structure (S30)

The final scores obtained for every subject profile matrix are suitably used in order to predict a protein three-dimensional structure. For example, a required procedure consists of the following known steps.

(1) Input Values

Firstly, as to a query profile matrix containing sequences to be predicted and a subject profile matrix containing model amino acid sequences each of which has a known three-dimensional structure, the final scores between both of the profile matrices and the lengths of the respective model sequences are inputted. At this time, if the subject profile matrix database includes N known model sequences, N final scores and N lengths of sequences are inputted.

(2) Compensation of Length Dependence in Final Scores

Because final scores between a query profile matrix containing sequences to be predicted and a subject profile matrix containing the respective known model sequences are deemed to depend on the lengths of the model sequences, they are subjected to the following statistical process. Firstly, plotting final scores between the query profile matrix containing sequences to be predicted and the profile matrix containing the respective known model sequences as the Y-axis with the values of natural logarithms of the lengths of the respective model sequences as the X-axis, a regression line is drawn with neglecting extraordinarily deviating values. Supposing that the regression line represents the value of an average final score at each length, each of the final scores between the query profile matrix containing sequences to be predicted and the subject profile matrix containing the respective known model sequences is estimated based on a deviation from the average value. Usually, as widely used, the degree of a deviation is determined using a standard deviation as a unit.

(3) Sorting

It is considered that a deviation from the average value the larger (on the side of a high score), a similarity the higher. Therefore, the measured results are sorted in a descending order of deviations from the average value (on the side of a high score) so as to be deemed candidates for a predicted structure.

(4) Outputting of Alignment and Scores as a Predicted Structure

The results are outputted in thus-sorted order as candidates for a predicted structure. Since it is meaningless to output all of the results, only a part of the results having a deviation from the average value, which exceeds a threshold determined empirically with consideration of prediction accuracy, are outputted. At this time, the degrees of deviations from the average value, which are calculated using a standard deviation as a unit, are displayed as indications of prediction accuracies.

As the results of alignment and final scores between the query profile matrix containing sequences to be predicted and the subject profile matrix containing the respective known model sequences, ones sequentially calculated through Dynamic Programming are outputted. Because each of the known model sequences has a known three-dimensional structure, this output of alignment gives the predicted result of a three-dimensional structure.

3. Computer Program

The present invention also provides a program for enabling a computer to function as a system for measuring the similarity between protein profile matrices in order to predict the three-dimensional structure of a protein. A program according to the present invention comprises the following means:

(a) means for preparing two profile matrices of a query profile matrix and a subject profile matrix;
(b) means for calculating correlation coefficients between the respective profile columns in said query profile matrix and the respective profile columns in said object profile matrix with respect to full or partial combinations of both of the respective profile columns; and
(c) means for forming a score matrix consisting of said correlation coefficients.

A program according to the present invention may comprise general-purpose means, which are usually included in a general-purpose program, other than the above-described indispensable means. As such means, listed are storage means for various sorts of data, information transmitter/receiver means, display/output means such as a display, a printer, etc., and so on.

4. Computer Recording Media

A program according to the present invention may be stored in a computer-readable recording medium or computer-accessible memory means. The present invention also covers a computer recording medium or memory means storing a program according to the present invention. As a recording medium or memory means, listed are a magnetic medium (a flexible disk, a hard disk, etc.), an optical medium (CD, DVD, etc.), a magneto-optical medium (MO, MD, etc.), and so on.

EXAMPLES

Referring to the following examples, a further detailed explanation of the present invention will be made below. However, these examples are not intended to limit the present invention in scope.

Example 1

(1) Makeup of Subject Profile Matrix Database

Model sequences were acquired from the classification data in the structure classification database SCOP (URL: http://scop. mrc-lmb. cam. ac. uk/scop/) release 1.59. Out of them, there were selected 948 amino acid sequences of proteins having a single domain and structural data with a resolution of 2.5 Å or less. Applying PSI-BLAST and the amino acid sequence database (acquired from NRDB; ftp://ftp. ncbi. nlm. nih. gov) to each of the 948 model sequences so as to form subject profile matrices, a complete subject profile matrix database was made up.

"NRDB" used here includes amino acid sequences of almost all proteins known at present. PSI-BLAST makes it possible to automatically collect sequences, which are considered to relate biologically to the respective model sequences, from NRDB and also to form a profile matrix.

(2) Formation of Query Profile Matrix

In order to check up whether or not a proper structure prediction is performed, sequences having known structures, i.e., the above-described 948 model sequences used for forming a subject profile matrix were used as sequences to be predicted. A query profile matrix was formed, sequentially using these sequences to be predicted, through the similar operations to those used for formation of a subject profile matrix, i.e., by applying PSI-BLAST and the amino acid sequence database (NRDB).

(3) Comparison Between the Respective Profile Matrices

Next, the query profile matrix containing the sequences to be predicted (in the present example, these are 948 model sequences), which were formed in item (2) above, was sequentially compared with each subject profile matrix in the subject profile matrix database. At that time, the respective components (similarity scores) in a score matrix obtained between both profile matrices were calculated using correlation coefficients between them.

With an input value of thus-obtained score matrix between the profile matrices, Dynamic Programming outputted final scores and an alignment.

The above-described operations for the query profile matrix were performed with respect to all of the subject profile matrices stored in the subject profile matrix database.

(4) Final Processing and Outputting of Results

In each of 948 predictions, the measured results were outputted according to the previously described ways. Specifically, the respective final scores between the query profile matrices and the subject profile matrices and the lengths of the respective model sequences were inputted so as to compensate the length-dependence of each final score. Then, they were sorted in a descending order of their deviations from the average value (on the side of a high score) and outputted in the sorted order as candidates for a predicted structure.

Figure 4:
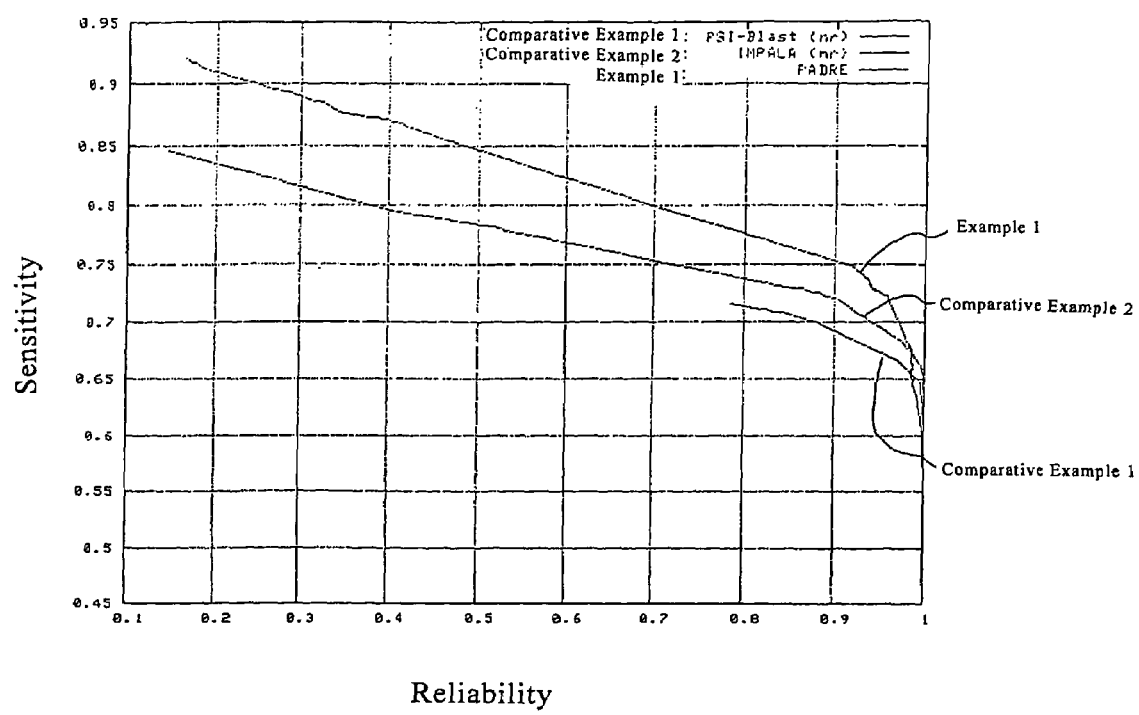
FIG. 4 is a graph plotting the values of reliability and sensitivity in the predicted results outputted in Example 1 and Comparative Examples 1 and 2.

Comparing thus-outputted candidates for a predicted structure with the already-known right structure, reliabilities and sensitivities of the respective predicted results were calculated and thus-calculated results were shown in FIG. 4.

Comparative Example 1

Using 948 model sequences which had been obtained in Example 1, a structure prediction was conducted through PSI-BLAST which had been generally used for searching the similarity of sequences. Specifically, with an input of a profile matrix formed by applying PSI-BLAST and an amino acid sequence database (acquired from NRDB; ftp://ftp. ncbi. nlm. nih. gov) to each of the 948 model sequences, a similarity search was made through the 948 model sequences and candidates for a predicted structure were outputted.

Comparing thus-outputted candidates for a predicted structure with the already-known right structure, reliabilities and sensitivities of the predicted results were calculated and the calculated results were shown in FIG. 4.

Comparative Example 2

Using 948 model sequences which had been obtained in Example 1, a structure prediction was conducted through IMPALA (Schaffer, A. A., Wolf, Y. I., Ponting, C. P., Koonin, E. V., Aravind, L., and Altschul, S. F. (1999) *Bioinformatics*. 015:1000-1011) which had been generally used for searching the similarity of sequences. Specifically, with inputs of 948 model sequences, a similarity search was made for each of the 948 model sequences through a previously made-up profile matrix database (using the subject profile matrix database made up in Example 1), and candidates for a predicted structure were outputted.

Comparing thus-outputted candidates for a predicted structure with the already-known right structure, reliabilities and sensitivities of the predicted results were calculated and the calculated results were shown in FIG. 4.

From FIG. 4, it is found that Example 1 according to the present invention is always superior to Comparative Examples 1 and 2 with respect to a sensitivity corresponding to a reliability in the range of 0.98 or less.

Comparative Example 3

Excepting that each component (a similarity score) in a score matrix between profile matrices was calculated by the dot product method (Rychlewski et al. (2000), 9: p232-241), candidates for a predicted structure were outputted in the same way as that in Example 1.

Figure 5:
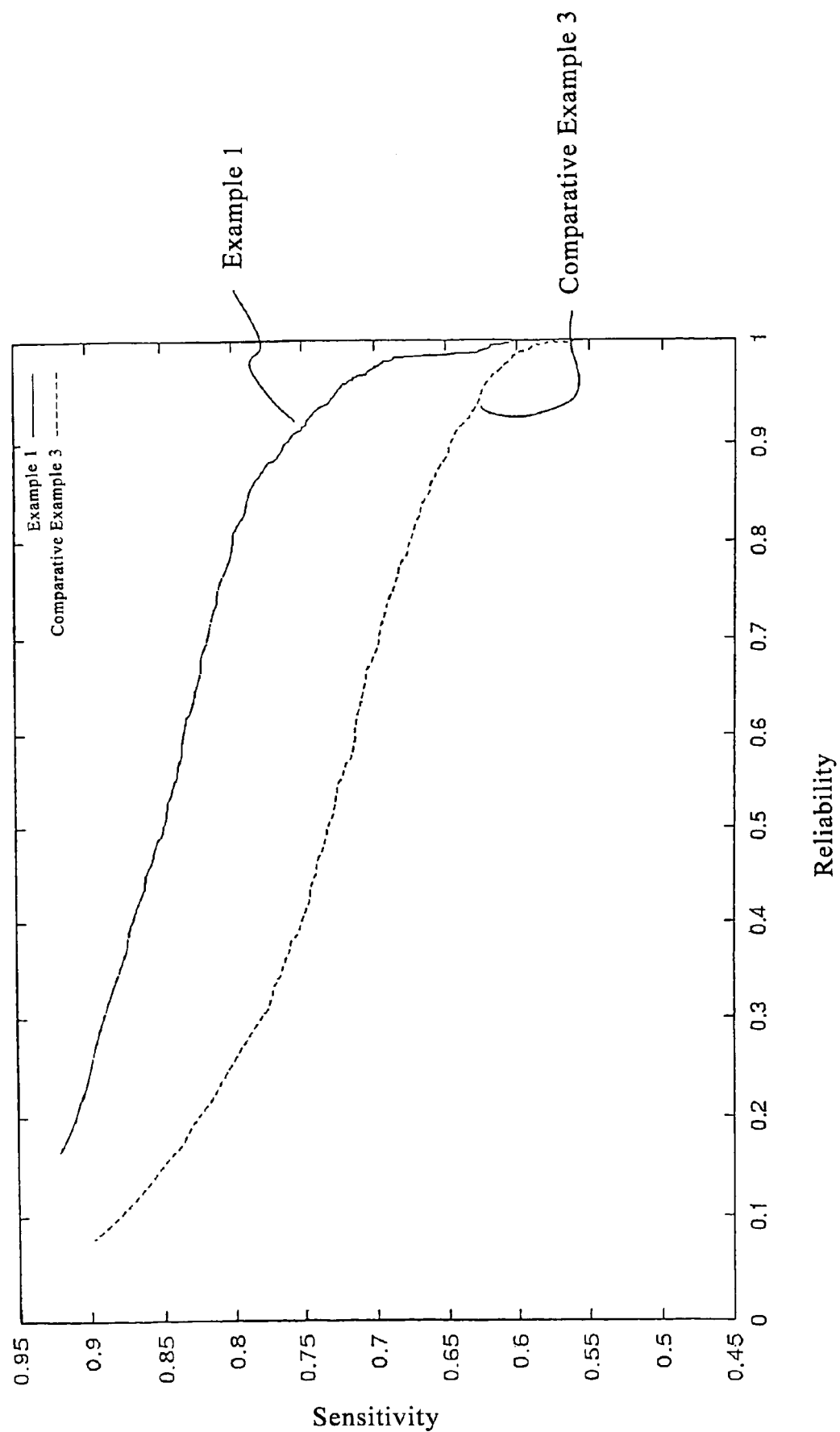
FIG. 5 is a graph plotting the values of reliability and sensitivity in the predicted results outputted in Example 1 and Comparative Example 3.

Comparing thus-outputted candidates for a predicted structure with the already-known right structure, reliabilities and sensitivities of the predicted results were calculated and the calculated results were shown in FIG. 5.

Example 2

(1) Makeup of Subject Profile Matrix Databases

Based on the classification data in the structure classification database SCOP (URL:http://scop. mrc-lmb. cam. ac. uk/scop/) release 1.59, 4381 model sequences of a single domain size, which contain mutually the same residues at a rate of less than 40%, were acquired from ASTRAL database (http://astral. stanford. edu/) which was the sequence database of SCOP. In addition, other sequences non-similar to the above-described 4381 sequences acquired from ASTRAL, which had been registered in the protein's tertiary structure database PDB (URL: http://www. rcsb. org/pdb/) but not ever registered in SCOP, were acquired in the following manners (A) to (D) and added to the model sequences. Using PSI-BLAST and NRDB, subject profile matrices were formed for every thus-selected amino acid sequences according to the following manners (A) to (D), whereby a complete subject profile matrix database was made up.

(A) Makeup of Subject Profile Matrix Database A

Applying BLASTP (Altschul et al., *Nucleic Acids Res.* (1997) 25(17): 3389-3402) to amino acid sequences in PDB at the time of May 18, 2002 with respect to model sequences based on the classification data in SCOP release 1.59, sequences having an expected value of 0.00001 or more were selected. Further putting them through a program blastclust for clustering of sequences, 248 sequences were selected such that they contain mutually the same residues at a rate of less than 40%. Using PSI-BLAST and NRDB at the time of May 18, 2002, subject profile matrices were formed for every one of 4629 sequences of thus-selected sequences plus 4381 model sequences based on the classification data in SCOP release 1.59, whereby a subject profile matrix database A was made up.

(B) Makeup of Subject Profile Matrix Database B

Applying BLASTP to the difference between amino acid sequences in PDB at the time of Jun. 23, 2002 and amino acid sequences in PDB at the time of May 18, 2002 with respect to the model sequences made up in item (A) above, sequences having an expected value of 0.00001 or more were selected. Further putting them through blastclust, 49 sequences were selected such that they contain mutually the same residues at a rate of less than 40%. Using PSI-BLAST and NRDB at the time of Jun. 17, 2002, subject profile matrices were formed for every one of 4678 sequences of thus-selected sequences plus the model sequences prepared in item (A) above, whereby a subject profile matrix database B was made up.

(C) Makeup of Subject Profile Matrix Database C

Applying BLASTP to the difference between amino acid sequences in PDB at the time of Jul. 14, 2002 and amino acid sequences in PDB at the time of Jun. 23, 2002 with respect to the model sequences made up in item (B) above, sequences having an expected value of 0.00001 or more were selected. Further putting them through blastclust, 23 sequences were selected such that they contain mutually the same residues at a rate of less than 40%. Using PSI-BLAST and NRDB at the time of Jul. 9, 2002, subject profile matrices were formed for every one of 4701 sequences of thus-selected sequences plus the model sequences prepared in item (B) above, whereby a subject profile matrix database C was made up.

(D) Makeup of Subject Profile Matrix Database D

Using PSI-BLAST and NRDB at the time of Aug. 6, 2002, subject profile matrices were formed for every one of 4701 sequences prepared in item (C) above, whereby a subject profile matrix database D was made up.

(2) Makeup of Query Profile Matrix Databases

For this purpose, used were the sequences which had been submitted to Structure Recognition Category (a prediction category for such a protein as has no clear sequence-similarity to proteins having known tertiary structures in usual sequence analyses but has a structure-similarity to known tertiary structures (when being actually analyzed), i.e., such a protein as presents some difficulty in its similarity search) in the fiscal 2002 session, CASP5/CAFASP3 (URL: http://predictioncenter.llnl.gov/casp5/), of Structure Prediction Contest held world-wide in alternate years, in other words, the amino acid sequences of such a protein as has no clear sequence-similarity to proteins having known tertiary structures in usual sequence analyses at present (e.g., PSI-BLAST etc.) and had been proved to have a structure-similarity to known tertiary structures (when being actually analyzed). Specifically, used were 22 amino acid sequences assigned with the following target numbers in URL:http://www.cs.bgu.ac.il/~dfischer/CAFASP3/targets.html:
T0130, T0132, T0134, T0135, T0136, T0138, T0146, T0147, T0148, T0156, T0157, T0159, T0162, T0168, T0170, T0172, T0173, T0174, T0186, T0187, T0191, T0193.

Using PSI-BLAST and NRDB, query profile matrices were formed for every one of these 22 sequences, whereby a complete query profile matrix database was made up.

In this connection, using four sorts of NRDBs at the respective times of May 18, 2002, Jun. 17, 2002, Jul. 9, 2002 and Aug. 6, 2002, the obtained query profile matrix databases were referred to as "a query profile matrix database A", "a query profile matrix database B", "a query profile matrix database C" and "a query profile matrix database D", respectively.

(3) Comparison Between the Respective Profile Matrices

Next, a query profile matrix in thus-made up query profile matrix database A containing sequences to be predicted and a subject profile matrix in the subject profile matrix database A were compared in the same manner as in item "(3) Comparison between The Respective Profile Matrices" above as to Example 1 (Comparison A).

Like operations were performed with respect to the respective combinations of query profile matrix database B and subject profile matrix database B, query profile matrix database C and subject profile matrix database C, and query profile matrix database D and subject profile matrix database D (Comparisons B, C and D, respectively).

(4) Final Processing and Outputting of Results

In each of 22 predictions, the measured results were outputted according to the previously described ways. Specifically, the respective final scores between query profile matrices and subject profile matrices, which were obtained in the respective database combinations (Comparisons A to D), and the lengths of the respective model sequences were inputted so as to compensate the length-dependence of each final score. Then, they were sorted in a descending order of their deviations from the average value (on the side of a high score) and highly-ranked 10 predictions in the sorted order were outputted as candidates for a predicted structure for every 22 sequences (Outputs A to D).

By comparing thus-outputted candidates for a predicted structure with three-dimensional structures which had been elucidated in a publicly-opened experiment after the lapse of a term for contributing a predicted structure to the contest, the accuracies of the predicted results were determined. In one method for evaluating a predicted structure, the predicted structure and its correct structure were overlapped and then the number of residues, from each of which the corresponding residue existed within a distance of shorter than 3 Å, was summed up for all of the outputs A to D (a sum value). As the result of studying 22 proteins from the point of view of structural domains as a unit (34 domains in total), the present method recorded a sum value of "577" when remarking one highly-ranked prediction for every one of the 22 sequences used in Structure Recognition Category of Structure Prediction Contest CASP5/CAFASP3. This showed that the present method was superior to any other method utilizing sequence information.

Also in the case wherein setting a certain threshold value to decide whether a prediction for some query sequence (to be predicted) was successful or unsuccessful, the present method recorded "9" as a value (a correct value) obtained by summing up the number of predictions decided to be successful for all of the outputs A to D. This showed that the present method was superior to any other method utilizing sequence information.

The invention claimed is:

1. A computer-based system for measuring the similarity between protein profile matrices stored in a computer readable medium to predict a protein three-dimensional structure, wherein each profile matrix comprises a group of profile columns containing occurrence probabilities of every amino acid type at a respective locations of amino acid residues in a multiple alignment in which amino acid sequences of a plurality of related proteins are multiply aligned, said system comprises:

(a) means for preparing and storing in the computer readable medium two profile matrices of a query profile matrix formed based on a plurality of proteins including proteins having three-dimensional structures to be predicted and a subject profile matrix formed based on a plurality of proteins having known three-dimensional structures retrieved from the computer readable medium;

(b) means for calculating and storing in the computer readable medium correlation coefficients between the respective profile columns in said query profile matrix and the respective profile columns in said subject profile matrix with respect to full or partial combinations of both the respective profile columns;

(c) means for forming a score matrix comprising said correlation coefficients and storing the score matrix in the computer readable medium; and (d) means for outputting at least one candidate for the predicted protein three-dimensional structure based on the results of the score matrix.

2. A system for predicting a protein three-dimensional structure characterized in using a score matrix formed through a system set forth in claim 1.

3. An executable program embodied in a computer readable medium for enabling a computer to function as a system for measuring the similarity between protein profile matrices to predict a protein three-dimensional structure, wherein each profile matrix comprises a group of profile columns containing occurrence probabilities of every amino acid type at a respective locations of amino acid residues in a multiple alignment in which amino acid sequences of a plurality of related proteins are multiply aligned, said system comprises:
- (a) means for preparing two profile matrices of a query profile matrix formed based on a plurality of proteins including proteins having three-dimensional structures to be predicted and a subject profile matrix formed based on a plurality of proteins having known three-dimensional structures;
- (b) means for calculating correlation coefficients between the respective profile columns in said query profile matrix and the respective profile columns in said subject profile matrix with respect to full or partial combinations of both the respective profile columns;
- (c) means for forming a score matrix comprising said correlation coefficients; and
- (d) means for outputting at least one candidate for the predicted protein three-dimensional structure based on the results of the score matrix.

4. A computer-readable recording medium storing a program set forth in claim 3.

5. A method for measuring the similarity between protein profile matrices to predict a protein three-dimensional structure, wherein each profile matrix comprises a group of profile columns containing occurrence probabilities of every amino acid type at a respective locations of amino acid residues in a multiple alignment in which amino acid sequences of a plurality of related proteins are multiply aligned, said method comprises:
- (a) preparing two profile matrices of a query profile matrix formed based on a plurality of proteins including proteins having three-dimensional structures to be predicted and a subject profile matrix formed based on a plurality of proteins having known three-dimensional structures;
- (b) calculating correlation coefficients between the respective profile columns in said query profile matrix and the respective profile columns in said subject profile matrix with respect to full or partial combinations of both the respective profile columns;
- (c) forming a score matrix comprising said correlation coefficients; and
- (d) outputting at least one candidate for the predicted protein three-dimensional structure based on the results of the score matrix.

* * * * *